United States Patent [19]

Higuchi et al.

[11] 4,188,951
[45] * Feb. 19, 1980

[54] INTRAUTERINE SYSTEM EMBRACING SELECTED COPOLYMERIC MEMBRANES FOR ADMINISTERING BENEFICIAL AGENT

[75] Inventors: Takeru Higuchi, Lawrence, Kans.; Anwar A. Hussain, Lexington, Ky.

[73] Assignee: Alza Corporation, Palo Alto, Calif.

[*] Notice: The portion of the term of this patent subsequent to Sep. 9, 1992, has been disclaimed.

[21] Appl. No.: 826,928

[22] Filed: Aug. 22, 1977

Related U.S. Application Data

[63] Continuation-in-part of Ser. No. 705,470, Jul. 7, 1976, Pat. No. 4,052,505, which is a continuation-in-part of Ser. No. 591,712, Jun. 30, 1975, abandoned, and a continuation-in-part of Ser. No. 281,446, Aug. 17, 1972, Pat. No. 3,903,880, which is a continuation-in-part of Ser. No. 80,531, Oct. 14, 1970, abandoned.

[51] Int. Cl.² .............................................. A61M 7/00
[52] U.S. Cl. .................................................... 128/260
[58] Field of Search .................... 128/260; 424/19, 21, 424/32, 33

[56] References Cited

U.S. PATENT DOCUMENTS

| | | | |
|---|---|---|---|
| 2,200,429 | 5/1940 | Perrin et al. | 526/235 |
| 2,396,785 | 3/1946 | Manford | 526/232 |
| 2,947,735 | 8/1960 | Bartl | 526/212 |
| 3,710,795 | 1/1973 | Higuchi et al. | 128/26 |
| 3,854,480 | 12/1974 | Zaffaroni | 128/260 |
| 3,896,819 | 7/1975 | Zaffaroni et al. | 128/260 |
| 3,903,880 | 9/1975 | Higuchi et al. | 128/260 |
| 3,911,911 | 10/1975 | Scommegna | 128/260 |

FOREIGN PATENT DOCUMENTS 569927 6/1945 United Kingdom.
582093 11/1946 United Kingdom.

OTHER PUBLICATIONS

Raff et al., Crystalline Olefin Polymers, Part II, pp. 261–266, 1964.
Fertility and Sterility, vol. 21, pp. 201–210, 1970, Scommegna et al.
Chemical Contraception, 1974, Columbia Press, pp. 58–61.

Primary Examiner—Robert W. Michell
Assistant Examiner—C. F. Rosenbaum
Attorney, Agent, or Firm—Paul L. Sabatine; Edward L. Mandell; Thomas E. Ciotti

[57] ABSTRACT

An intrauterine system for releasing beneficial agent to the uterus at a controlled and continuous rate for a prolonged period of time is disclosed. The system is shaped, sized and adapted for insertion and retention in the uterus. The system contains a beneficial agent and it is formed of a copolymeric material permeable to the passage of agent by diffusion. The material is an ethylene-vinyl ester polymer of the general formula:

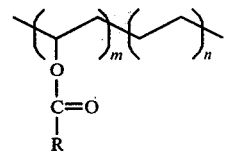

wherein R is hydrogen, alkyl of 2 to 7 carbons, or aryl, m is (4 to 80)% by weight and n is (100-m)% by weight.

12 Claims, 5 Drawing Figures

4,188,951

INTRAUTERINE SYSTEM EMBRACING SELECTED COPOLYMERIC MEMBRANES FOR ADMINISTERING BENEFICIAL AGENT

CROSS-REFERENCE TO RELATED APPLICATIONS

This application is a continuation-in-part of U.S. patent application Ser. No. 705,470 filed on July 7, 1976, and now U.S. Pat. No. 4,052,505 issued on Nov. 4, 1977, which application is a continuation-in-part of U.S. patent application Ser. No. 591,712 filed on June 30, 1975 now abandoned; said application Ser. No. 591,712 a continuation-in-part of U.S. patent application Ser. No. 281,446 filed on Aug. 17, 1972, and now U.S. Pat. No. 3,903,880, which application is a continuation-in-part of U.S. patent application Ser. No. 80,531 filed on Oct. 14, 1970, now abandoned. These applications are assigned to the same assignee of this application, and benefit of all their filing dates is claimed.

FIELD OF THE INVENTION

This invention relates to a novel and useful intrauterine delivery system for releasing a pharmaceutically acceptable beneficial agent at a controlled and continuous rate for a prolonged period of time to the uterus to produce a desired physiological or pharmacological effect. The intrauterine delivery system is comprised of a drug release rate controlling copolymeric material surrounding at least a part of the drug, or the material contains the drug therein. The material is permeable to the passage of drug by diffusion.

BACKGROUND OF THE INVENTION

Often, in the medical and veterinary programs, it is desirable and important to provide for the slow release of a beneficial agent such as a drug to the uterus at a controlled and continuous rate over a prolonged period of time. In many programs, such a rate of release should be substantially constant or have a zero order time dependence, that is, the rate of release is independent of time. For example, in contraception, it has been found that fertility can be regulated by release of the steroid progesterone to the uterus from a device inserted in the uterine lumen; with release of progesterone from the device at a constant rate for a prolonged period, a convenient long-term birth control procedure is provided.

Different approaches have heretofore been tried to obtain a delivery device for releasing drug at a controlled rate. One approach, which has received great attention, is to mix the drug with a carrier material that is gradually broken down by body fluids, the drug being released as the carrier disintegrates. Numerous carriers have been used in such systems including waxes, oils, fats, soluble polymers and the like. While some of these systems have provided for a delayed release of the drug, constant release rate has not been obtained. One reason for this is that as the carrier disintegrates the surface area of the dosage unit decreases, concomitantly exposing increasingly smaller quantities of the carrier to the surrounding body fluids. This inherently results in a decline in the release rate over time. Moreover, there has been little success in gaining control over drug release rate by this approach.

Another approach has been to enclose the drug within a capsule having polymeric walls through which the drug can pass by diffusion. An approach of this kind is set forth in U.S. Pat. No. 3,279,996. These devices too have inherent difficulties. These prior systems have generally been based on the use of silicone rubber polymers, especially polydimethylsiloxanes, as the diffusion control membrane. In large part, these silicone polymers were selected because of their high permeability to some important drug molecules. But it has now been found that this high permeability can be a significant disadvantage which defeats the primary objective of an acceptable and useful drug delivery device. Thus, with many important drug molecules, such as progesterone, the diffusion rate through polydimethylsiloxane membranes is very great, often greater than the rate of clearance of the diffused drug from the outer surface of the capsule. In many instances, this results in the rate limiting step being clearance of the drug from the exterior of the capsule, rather than diffusion through the capsule wall. Clearance rate within the body is difficult to control, as it is subject to frequent changes and, when it is the rate-limiting step, the objective of providing a drug delivery device which releases drug at a constant rate over time cannot be obtained. Also, silicone rubbers have a tendency to absorb lipoidal materials from the body. When this effect occurs in vivo, the nature of the membrane changes, altering the release rate. Still another problem with the silicone rubber dosage forms is the difficulty encountered in fabrication, attributable largely to the silicone rubber itself, that is, it is not thermoplastic and accordingly it does not lend itself to the manufacture of heat sealed drug delivery devices. While the above-mentioned polymer, silicone, has been found to have too high a permeability to many therapeutic drugs to lend itself to successful use as a drug release rate controlling barrier, in other instances, polymers such as poly(ethylene), which is thermoplastic and has a high degree of crystallinity, has also been found to have too high a melting point that can adversely affect the drug during fabrication of the device, and because its crystallinity has too low a permeability to drug to be successfully used as a drug release rate barrier.

In unrelated, non-uterine fields, polymeric materials have been used for releasing non-uterine substances. For example, in U.S. Pat. No. 3,310,235 a device is disclosed made of the material ethylene-vinyl acetate copolymer, as seemingly suitable for releasing volatile, organic and toxic phosphorous biocides by the process of physical evaporation. With this device, biocide release is achieved by evaporation from the surface, and if the ingredient is not sufficiently volatile at the temperature of use, the device has no practical value. Evaporation is achieved by using a woven cloth which acts as an evaporation surface. Release rate by evaporation is difficult to regulate and virtually impossible to control, as it is subjected to uncontrollable environmental conditions, the vapor pressure of the substance, and the degree of saturation of the volatile substance in the environment. This type of clearance inherently defeats the basic purpose of providing a device for uterine use which requires release of agent at a controlled and continuous rate for a prolonged period of time as by the process of diffusion. Other incidental and non-therapeutic uses for ethylene-vinyl acetate copolymer are disclosed in U.S. Pat. No. 3,400,011 wherein the polymeric material is mixed with waxes and used for coating ingredients that are substantially released by the movement of external fluids into the coating, causing it to rupture and release the ingredient; in French Pat. No. 1,489,490 as a thickener; and in French Pat. No.

1,505,267 as a non-diffusional formless base for chewing gum. In our U.S. Pat. No. 3,903,880 issued Sept. 9, 1975 delivery devices manufactured from ethylene-vinyl acetate copolymer are disclosed for releasing drugs at controlled rates to animals. The devices claimed in said patent are intrauterine devices and they are used for releasing agent to the uterus. In this application, it has now been found that other ethylene-vinyl ester copolymers can be inventively used for manufacturing intrauterine systems designed in the form of an intrauterine device for releasing a beneficial agent to the uterus at a controlled rate over a prolonged period of time.

OBJECTS OF THE INVENTION

One important object of this invention is to provide a novel and useful shaped drug delivery system manufactured in the form of an intrauterine device for use in the uterus for prolongedly releasing drug at a controlled rate, by providing a copolymeric material that has the ability to give therapeutically operable drug release rates in the uterus while simultaneously remaining substantially free of any adverse unwanted toxic effects in the host.

Still another object of this invention is to provide a medical and veterinary useful intrauterine delivery system which can release a beneficial agent at a rate which does not vary with time.

Yet a further object of this invention is to provide an intrauterine drug delivery system fabricated from a material which is compatible with body tissue and exhibits substantially no toxicity thereto.

Still yet another object of the invention is to provide a reliable and easily used intrauterine drug delivery system for continuously administered controlled quantities of drug to the uterus and to its receptor sites.

Still a further and immediate object of this invention is to provide an intrauterine drug delivery system for the administration of a locally acting or systemically acting uterine drug to produce a physiological or pharmacological effect.

Still another object of the invention is to provide an intrauterine delivery system made from a material that can be handled, for example, heat sealed, without substantially adversely effecting the properties of the drug, particularly a uterine drug as contained therein.

Yet a further object of the invention is to provide an intrauterine system designed as an intrauterine device and formed of a drug release rate controlling copolymeric material permeable to the passage of drug by diffusion which process is the drug release rate controlling means for releasing drug from the system.

Other objects of this invention will become more apparent to those skilled in the art from the following detailed description of the invention, taken in conjunction with the drawings and the accompanying claims.

SUMMARY OF THE INVENTION

In accomplishing the objects, features and advantages of this invention, it has now been found that an intrauterine system for releasing a beneficial agent such as a drug over a prolonged period of time comprising a reservoir and a polymeric barrier through which the agent passes by diffusion, can be provided by using an ethylene-vinyl ester copolymer as the copolymeric material. In a presently preferred embodiment, the invention resides in an intrauterine dispensing device which is a flexible body of an ethylene-vinyl ester copolymer having a vinyl ester content of about 4 to 80% by weight. The system contains an agent which is dispensed to the uterus by diffusion through the copolymer. The system is adapted for insertion in the uterus over a prolonged period of time.

BRIEF DESCRIPTION OF THE DRAWINGS

In the drawings, which are not drawn to scale, but are set forth to illustrate various embodiments of the invention, the figures are as follows.

In the drawings and specifications, like parts in related figures are identified by like numbers. The terms appearing earlier in the specification and in the description of the drawings, as well as embodiments thereof, are further described elsewhere in the disclosure.

DETAILED DESCRIPTION OF THE DRAWINGS

In accordance with this invention, it has now been unexpectedly found that ethylene-vinyl ester copolymers can be successfully manufactured into novel and useful intrauterine delivery system and can therefore be used for the controlled release of agent to the uterus by diffusion.

Figure 1:
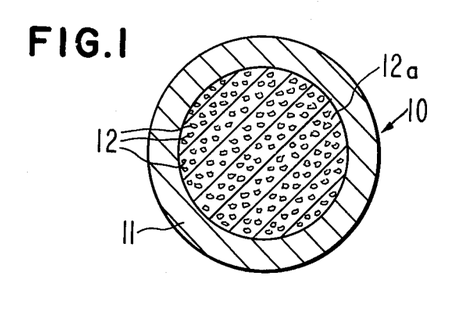
FIG. 1 is a side cross-sectional view of an intrauterine drug delivery system of the invention comprised of a wall surrounding a reservoir containing drug.
Figure 2:
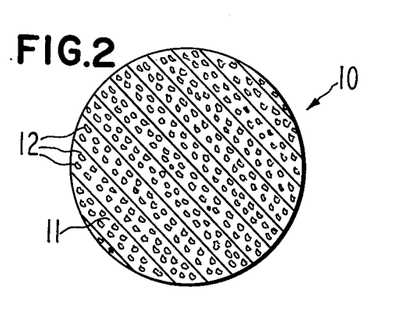
FIG. 2 is a side cross-sectional view of another embodiment of the drug delivery system of the invention comprised of a system having drug therein.

As illustrated in FIG. 1, the novel and useful intrauterine delivery system 10 of the invention can have a wall 11 fabricated of ethylene-vinyl ester copolymer enclosing a reservoir 12a containing a beneficial agent such as a drug 12. Agent 12 is capable of diffusing through ethylene-vinyl ester copolymer walls 11. Alternatively, as illustrated in FIG. 2, intrauterine delivery system 10 can be comprised of a solid matrix 11 of ethylene-vinyl ester copolymer, which also serves as a drug reservoir 12a, having drug 12 distributed therethrough.

Figure 3:
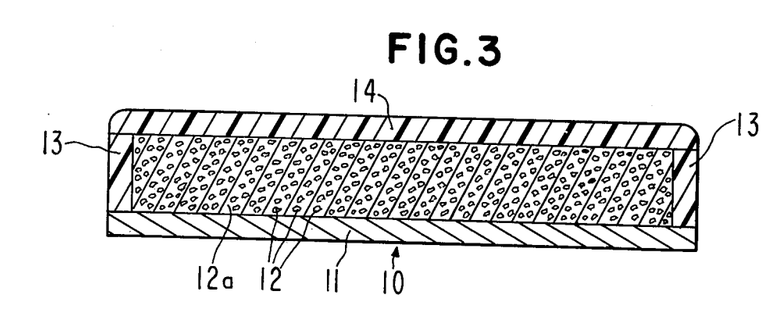
FIG. 3 is a side cross-sectional view of another embodiment of the invention in the form of a rectangular system.

Essential to this invention is the use of an ethylene-vinyl ester copolymer as the rate limiting barrier for the controlled and continuous release of agent and drug by diffusion. This requires the intrauterine system have at least one barrier or wall of biologically acceptable ethylene-vinyl ester copolymer through which the agent will pass by diffusion. Various forms of the invention are included within this framework. Thus, the system of the invention can have a single ethylene-vinyl ester copolymer membrane on one surface thereof and through which the drug will pass by diffusion. One form of this embodiment is illustrated in FIG. 3, a detailed description of which is presented later in the specification. In another embodiment of the invention, the intrauterine system is a biologically acceptable container, with walls of ethylene-vinyl ester copolymer, and the drug in the interior thereof; see FIG. 1 for example. In this form of the invention, drug alone can be within the interior reservoir of the system or the drug can be dispersed in a liquid, semi-solid, or solid matrix and the matrix enclosed within the ethylene-vinyl ester copolymer barrier. In each of these embodiments, passage of the drug by diffusion through the ethylene-vinyl ester copolymer is the rate controlling step for drug administration. For further details of such a drug delivery system in which the drug is dispersed throughout a solid matrix enclosed within a barrier through which drug can pass by diffusion, reference is made to U.S. Pat. No. 3,854,480 for an invention of Alejandro Zaffaroni assigned to the assignee of this invention. The disclosure of that application is relied upon and incorporated herein by reference. In another embodiment of the invention (as in FIG. 2), the drug 12 is distributed throughout a matrix, which matrix in this embodiment is a reservoir 12a, of ethylene-vinyl ester copolymer 11. Preferably, solid particles or a liquid form of the drug are used, although the drug can be in solution in the copolymeric matrix.

The intrauterine delivery systems of the invention can take a wide variety of shapes and forms for administering the drugs to the uterus at controlled and continuous rates. In each instance, the delivery system has an ethylene-vinyl ester copolymer barrier for release of the drug by diffusion. For example, as illustrated in FIG. 3, rectangular shaped system 10 is comprised of a film 11 of ethylene-vinyl ester copolymer on one surface of a reservoir 12a containing drug 12. The reservoir is bounded by side walls 13 and top surface wall 14. This system is shaped, sized and adapted to release drug in the uterus by diffusion through film 11 at a predetermined rate.

Figure 4:
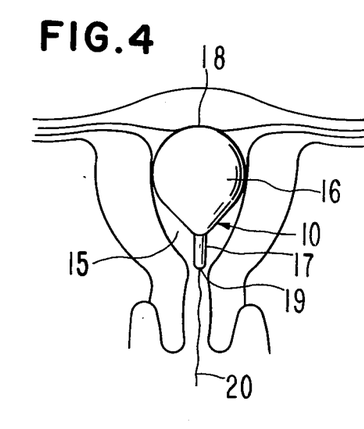
FIG. 4 is a view illustrating an intrauterine delivery system having a tear-drop shape and a dependent member therefrom; and, FIG. 5 is a cross-sectional view of an intrauterine system manufactured with a reservoir.

FIG. 4 illustrates an intrauterine system 10 positioned in uterus 15 with system 10 releasing agent 12 thereto over a prolonged period of time. The phrase "intrauterine system," as used herein embraces "intrauterine therapeutic device" when it releases a beneficial drug, "intrauterine device" when it releases a drug or a contraceptive agent, and "intrauterine contraceptive device" when it releases a contraceptive agent. In FIG. 4, system 10 is seen positioned in uterine cavity 15 and it, system 10, consists essentially of a tear-drop shaped member 16 suitably fixed to a dependent member 17. System 10 has a lead end 18 and a distant end 19. System 10 is sized, shaped and adapted to fit all uterine cavities. Its dimensions can be made to conform to the nulliparous and multiparous cavities. Generally, member 16 will have a width of 20 to 40 millimeters, a length of 20 to 40 millimeters, and a thickness of 1 to 4 millimeters. System 10 for the purpose of this invention is manufactured with steroid releasing means, not shown in FIG. 4. The releasing means can comprise steroid distributed throughout the system formed of the copolymeric esters, or the steroid can be housed in a reservoir within the system.

Figure 5:
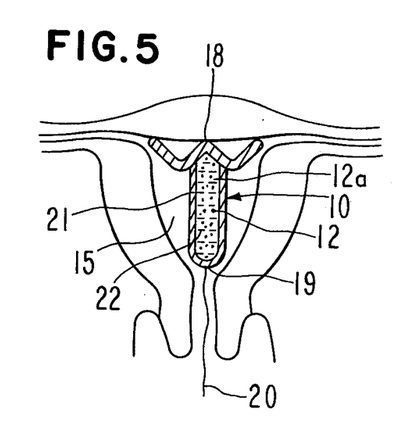

FIG. 5 illustrates an intrauterine system made with a reservoir 12a for housing a progestational or estrogenic steroid 12. System 10 is seen in opened, cross-section with reservoir 12a formed by a wall 21 of the copolymeric esters surrounding reservoir 12a. Reservoir 12a is an internal space and it contains a steroid 12 and a carrier 22 permeable to the passage of steroid 12. Wall 21 is formed of the steroid release rate controlling copolymer permeable to the passage of steroid 12, but at a lower rate than through carrier 22. In operation, steroid 12 dissolved in carrier 22 is released from system 10 by diffusion through wall 21 at a rate controlled by wall 21. System 10 is equipped with a string 20 for pulling system 10 from uterus 15. One important advantage in using ethylene-vinyl ester copolymers in such intrauterine dispensing systems is that precise control over the rate of release of beneficial agents such as drugs and anti-fertility steroids is obtained with the agent being released at a therapeutically or contraceptively effective rate.

DETAILED DESCRIPTION OF THE INVENTION

In accordance with the practice of this invention, it has now been found the polymeric material ethylene-vinyl ester copolymers of the general formula:

wherein R is hydrogen, lower alkyl of 2 to 7 carbons and aryl, and m is (4 to 80)% by weight and n is (100-m)% by weight, can be successfully used to provide intrauterine delivery devices. Typical alkyl groups include ethyl, propyl, isopropyl, butyl, tert-butyl, pentyl and hexyl. Typical aryl groups include phenyl and benzyl.

The ethylene-vinyl ester copolymers are made by the copolymerization of ethylene with vinyl esters of the formula wherein R is as defined.

Typical esters, named as the substituted acetate, include: vinyl formate vinyl butyl acetate also known as vinyl hexanoate; vinyl methyl acetate also known as vinyl propionate; vinyl ethyl acetate also known as vinyl butyrate; vinyl propylacetate also known as vinyl pentanoate; vinyl trimethylacetate vinyl diethylacetate also known as 2-ethylbutanoate, vinyl isopropylacetate also known as 3-methylbutanoate; vinyl tert-butylacetate also known as 3,3-dimethylbutanoate; vinyl phenylacetate and, vinyl benzoate Representative ethylene-vinyl ester copolymers suitable for providing ocular devices, with the copolymers named as acetates, include ethylene-vinyl formate, ethylene-vinyl butyl acetate, ethylene-vinyl methylacetate, ethylene-vinyl ethylacetate, ethylene-vinyl propylacetate, and the like.

Ethylene-vinyl ester copolymers are well known commercially available materials. Exemplary techniques for their preparation are described in U.S. Pat. Nos. 2,200,429, 2,396,785, and 2,947,735, in British Pat. Nos. 569,927 and 582,093, and in *Crystalline Olefin Polymers,* Editors Raff, R. A. V., and Doak, K. W., Part II, pages 261 to 266, 1964, published by Interscience Publishers, New York. In its broadest aspects, the present invention contemplates use of ethylene-vinyl ester copolymers and preferably, ethylene-vinyl ester copolymers having a vinyl ester content of about 4 to 80% by weight of the total, a melt index of about 0.1 to 1000 grams per ten minutes, a density of 0.120 to 1.25, and a frequency of acyloxy groups (RCO) on the polyethylene backbone of 1/200 to 1/3.5. In a preferred embodiment, the ethylene-vinyl ester copolymer has a vinyl ester content of about 4 to 50% by weight, a melt index of about 0.5 to 500 grams per ten minutes, a density having a range of about 0.920 to 1.190, and a frequency of acyloxy groups on the polyethylene backbone of 1/150 to 1/8. More preferably, the copolymer has a vinyl ester content consisting essentially of 4 to 40% by weight and a melt index of about 0.5 to 25 grams per ten minutes. Moreover, it has been surprisingly found that the absolute release rate of agent through these ethylene-vinyl ester copolymer barriers can be varied and accurately controlled by selecting a copolymer having the frequency of acyloxy groups with an alkyl moiety of 2 to 7 carbons within the range set forth above. Melt index is the number of grams of copolymer which can be forced through a standard temperature and thus is inversely related to a molecular weight. As used in this specification and the appended claims, melt index is as determined in accordance with standard ASTM D 1238-65T condition E practice.

The ethylene-vinyl ester copolymers and preferably the ethylene-vinyl lower alkyl substituted acetate copolymer, act as the rate controlling barrier as they are permeable to drugs, and they permit passage of the drug by diffusion through the copolymer at a relatively low to relatively high rate. Normally, the rate of passage of the drug through the copolymer is dependent on the solubility of the drug therein, as well as on the thickness of the polymeric barrier. This means that selection of particular copolymers, such as ethylene-vinyl ester compositions, will be dependent on the particular drug to be used. By varying the composition and thickness of the rate controlling barrier, the dosage rate per area of the system can be controlled; as the copolymer acts to meter the flow or diffusion of drug to the exterior of the device. Thus, systems of the same surface area can provide different dosage of a drug by varying the characteristics of the copolymer.

In addition to varying the percentage of vinyl ester, such as vinyl methyl acetate in the copolymer and the melt index or molecular weight, the properties of the copolymer can be changed by selectively hydrolyzing for example a portion of the acyloxy groups to alcohol groups. That is, by converting a preselected portion of the vinyl ester units of the copolymer to vinyl alcohol units, the copolymer is rendered more hydrophilic and the rate of passage of relatively hydrophilic drug molecules is increased. The percentage of units hydrolyzed to vinyl alcohol units can vary widely, but typically, from about 20 to 60% are converted. This partial hydrolysis is a well known procedure and can be accomplished under standard conditions well known in themselves. Exemplary hydrolysis procedures are set forth in U.S. Pat. Nos. 2,386,347, 2,399,653, 3,386,978, 3,494,908, and the like.

Permeability of the copolymers to drugs by diffusion also can be varied by incorporating fillers into the copolymer. Typical fillers that can be employed in practice of the invention are silica, clay, barytes, carbon black, lithopone, zinc oxide, etc. It should be realized that use of many of these fillers will affect the melt index of the copolymer. However, when melt index is used herein to define the copolymer, it is used as a measure of molecular weight and refers to the melt index of the particular copolymer composition without any filler present. Additionally, in those instances where the rate of release of drug is less than a preselected rate, the drug can be converted to known derivatives that have a greater permeability of drug through the membrane to increase the rate of release. Also, where the rate of drug diffusion is too slow, the rate can easily be increased by using drug delivery devices as embodied in FIG. 2.

Selection of the particular copolymer is governed in large part by the agent or drug to be incorporated in the system, as well as by desired rate of release thereof. Those skilled in the art can readily determine the rate of diffusion of drugs through these copolymers are select suitable combinations of copolymer and drug for particular applications. Various techniques can be used to determine the permeability of the copolymers to different drugs. One that has been found to be eminently well-suited is to cast or hot press a film of the copolymer to a thickness in the range of 2 to 60 mils. The film is used as a barrier between a rapidly stirred (e.g. 150 r.p.m.) saturated solution of the drug and a rapidly stirred solvent bath, both maintained at constant temperature (typically 37° C.). Samples are periodically withdrawn from the solvent bath and analyzed for drug concentration. By plotting drug concentration in the solvent bath versus time, the permeability constant P of the film is determined by the Fick's First Law of Diffusion.

$$\text{Slope of plot} = \frac{Q_1 - Q_2}{t_1 - t_2} = p\frac{AC}{h}$$

wherein $Q_1$=cumulative amount of drug in solvent in micrograms at $t_1$, $Q_2$=cumulative amount of drug in solvent in micrograms at $t_2$; $t_1$=elapsed time to first sample, i.e., $Q_1$; $t_2$=elapsed time to second sample, i.e., $Q_2$; a=area of film in cm$^2$; C=initial concentration of drug in saturated solution at t; h=thickness of film in cm. By determining the slope of the plot, i.e., $$\frac{Q_1 - Q_2}{t_1 - t_2},$$

and solving the equation using the known or measured values of A, C, and h, the permeability P constant in cm$^2$/time of the film for a given drug is readily determined. Of course, this permeability constant is an inherent characteristic of a copolymer of particular composition and melt index, and is unchanged whether the material is used as a matrix or as a film wall. The procedures used to determine the rate of drug release through the copolymer can easily be ascertained by standard techniques known to the art as recorded in *J. Pharm. Sci.*, Volume 52, pages 1145 to 1149, 1963; ibid., Volume 53, pages 798 to 802, 1964; ibid., Volume 54, pages 1459 to 1464; 1965; ibid., Volume 55, pages 840 to 843, and 1224 to 1239, 1966; *Encyclopedia of Polymer Science Technol.* Volume 5 and 9 pages 65 to 82, and 794 to 807, 1968; the references cited therein, and the like.

The rate of solubilization, or the rate at which drug will go into solution or dissolve in a vehicle confined within the reservoir is quantitatively governed by known physico-chemical principles. For an example, a drug particle dispersed in a vehicle is surrounded by a thin layer of vehicle having a finite thickness l in cm. This layer is considered as an integral part of the drug and it is characteristically referred to as the "stagnant layer". The stagnant layer remains a part of the surface of the drug, moving wherever the drug moves. Using Fick's First Law of Diffusion, the rate of solution is the rate at which a dissolved drug diffuses through the stagnant layer for supplying drug to the drug device's reservoir's inner wall. The driving force behind the movement of the drug through the stagnant layer is the difference in concentration of the drug, $C_1$, in the stagnant layer at the surface of the drug, and the concentration $C_2$ on the farthest side of the stagnant the drug, and the concentration $C_2$ on the farthest side of the stagnant layer. The difference in concentration $C_1-C_2$ determines the rate at which drug is solubilized in the vehicle. Hence, if the vehicle on the farthest side contains its optimum concentration because of a low release by the drug release rate controlling wall, the rate of solubilization of new drug will be low. Correspondingly, as drug leaves the vehicle, new drug is solubilized to establish a steady state within the vehicle.

The rate of diffusion of a drug in the vehicle comprising the reservoir, is broadly determined by measuring the rate of a drug transferred from one chamber through a sintered glass filter of known pore size and thickness into another chamber and calculating from the obtained data the drug transfer rate. The method is carried out by adding to a first conical flask equipped with a ground glass stopper and a stirring bar, a measured amount of vehicle and simultaneously, the drug in the same vehicle is added to a second conical flask while keeping the level of the vehicle in the two flasks the same. Next, the flasks are stirred and samples drawn at various time intervals for analysis. The measured rate of drug transport through the sintered glass filter, and the concentration difference of the drug in the two flasks is then calculated. These procedures are known to the art in *Proc. Roy. Sci. London,* Series A, Volume 148, page 1935; *J. Pharm. Sci.,* Volume 55, pages 1224 to 1229, 1966; and references cited therein. The diffusion coefficient of a drug can also be experimentally determined by using the above apparatus or similar apparatus and procedures as described in *Diffusion in Solids, Liquids and Gases,* by W. Jost, Chapter XI, pages 436 to 488, 1960, Revised Edition, Academic Press Inc., New York.

The solubility of a drug in the drug release rate controlling copolymer material comprising the wall of a drug delivery system broadly is determined by preparing a saturated solution of a given drug and ascertaining, by analysis, the amount present in a difinite area of the copolymer material. For example, the solubility of the drug in the wall is determined by first equilibrating the wall material with a saturated solution of the drug at a known temperature, for example 37° C., or with a pure liquid drug, if the drug is a liquid at 37° C. Next, drug is desorbed from the saturated wall material with a suitable solvent for the drug. The resultant solution for the drug then is analyzed by standard techniques such as ultraviolet, visible spectrophotometry, refractive index, polarography, electrical conductivity and the like, and calculating from the data the concentration or solubility of the drug in the material.

The solubility of a drug in a vehicle can be determined by various art known techniques. One method consists in preparing a vehicle, of the given drug and ascertaining by analysis the amount of drug present in a definite quantity of the vehicle. A simple apparatus for this purpose consists of a test tube of medium size fastened upright in a water bath maintained at constant temperature. The vehicle and drug are placed in the tube and stirred by means of a motor driven rotating glass spiral. After a given period of stirring, a definite weight of the vehicle is analyzed and the stirring continued for an additional period of time. If the analysis shows no increase of dissolved substance after the second period of stirring, the results are taken as the degree of solubility of the drug in the vehicle. Numerous other methods are available for the determination of the degree of solubility of a drug in a vehicle. Typical methods used for the measurement of solubility are chemical analysis, measurement of density, refractive index, electrical conductivity, and the like. Details of various methods for determining solubilities are described in United States Public Health Service Bulletin No. 67 of the Hygenic Laboratory; *Encyclopedia of Science and Technology*, Volume 12, pages 542 to 556, 1971, McGraw-Hill Inc.; *Encyclopaedic Dictionary of Physics*, Volume 6 pages 545 to 557, 1962, Pergamon Press Inc.; and the like.

Also, according to Fick's Law, the rate of drug solution is directly proportional to the area of the drug, A in cm$^2$, as exposed to vehicle and inversely proportional to the length of the path through which the dissolved drug molecule must diffuse. Then, the rate of solution of the drug is given by:

$$R = \frac{DA}{l}(C_1 - C_2)$$

wherein R is the rate of solution, D is a proportionality constant called diffusion coefficient in cm$^2$/sec, and $C_1$, $C_2$, and $l$ are as previously defined. See *Remington's Pharmaceutical Science*, 14th Edition, pages 246 to 269, 1970, Mack Publishing Company.

In practicing the invention, one can employ agent or drug used to treat the uterus or for controlling fertility by employing agent capable of diffusing through a copolymer at an effective rate. Suitable agents for use in the intrauterine delivery system of the invention include, without limitation, drugs that produce a physiologically or pharmacologically localized or systemic effect, and a contraceptive effect in animals, including warm blooded mammals, human and primates, valuable domestic household, sport or farm animals such as horses, dogs, cats, cattle, sheep and the like; or for administering to laboratory animals such as mice, monkeys, rats, rabbits and guinea pigs. The active drugs that can be administered by the novel drug delivery system of the invention include, without limitation: anti-fertility agents, which broadly includes progestational substances, estrogenic substances and mixtures thereof, that have anti-fertility properties. These substances can be of naturally occurring or synthetic origin and they generally possess a cyclopentanophenanthrene nucleus. The term progestational substance as used herein embraces "progestogen" which term is used in the steroid art to generically describe steroids possessing progestational activity, and the former also includes "progestins", a term widely used for synthetic steroids that have progesteroid effects. The active anti-fertility agent that can be used to produce the desired effects in female mammals, including humans and primates that are able to maintain control of the reproduction process, include without limitations: pregn-4-ene-3,20-dione (also known as progesterone); 19-nor-pregn-4-ene-3,20-dione; 17-hydroxy-19-nor-17α-pregn-5(10)-ene-20-yn-3-one; dl-11β-ethyl-17-ethinyl-17-β-hydroxygon-4-ene-3-one; 17α-ethinyl-17-hydroxy-5(10)-estren-3-one; 17α-ethinyl-19-norestosterone; 6-chloro-17-hydroxypregna-4,6-diene-3,20-dione; 17β-hydroxy-6α-methyl-17-(1-propynyl)androst-4-ene-3-one; 9β,10α-pregna-4,6-diene-3,20-dione; 17-hydroxy-17α-pregn-4-en-20-yne-3-one; 19-nor-17α-pregn-4-en-20-yne-3β,17-diol; 17-hydroxypregn-4-ene-3,20-diene; 17-hydroxy-6α-methylpregn-4-ene-3,20-dione; 17-hydroxy-pregn-4-ene-3,20-dione; 17-α-hydroxyprogesterone; mixtures thereof, and the like.

The term estrogenic and estrogenic anti-fertility agents as used herein also includes the compounds known as estrogens, and the metabolic products thereof that possess anti-fertility properties or are converted to active anti-fertility agents in the preselected biological environment. Exemplary estrogenic compounds include β-estradiol, β-estradiol 3-benzoate, 17-β-cyclopentanepropionate estradiol, 1,3,5(10-estratnene-3,17β-diol dipropionate, estra-1,3,5(10-triene-3,17-β-diol-valerate, estrone, ethinyl estradiol, 17-ethinyl estradiol-3 methyl ether, 17-ethinyl estradiol-3-cyclopentoether, estriol, mixtures thereof, and the like.

Additional agents or drugs that can be delivered by the device to the uterus include antibiotics such as tetracycline; antibacterials such as sulfonamides; anti-inflammatories such as dexamethasone; hormonal agents such as prostaglandin F$_{2\alpha}$; and the like.

Drugs contained in the reservoir can be in different forms, such as uncharged molecules, components of molecular complexes or non-irritating, pharmacologically acceptable derivatives thereof. For simple derivatives of the drugs such as pharmaceutically acceptable ethers, esters, amides, and the like which have desirable retention and release characteristics but which are easily hydrolyzed by uterine pH, converted by uterine enzymes to active forms, and the like, can be employed.

The amount of drug incorporated in the intrauterine system varies depending on the agent or drug, the desired effect, and the time span for which the system provides therapy or contraception. Since a variety of systems are intended to provide dosage regimes for therapy and contraception, there is no critical upper limit on the amount of agent incorporated in the system. The lower limit too will depend on the activity of the agent and the time span of its release from the system. Thus, it is not practical to define a range for the therapeutically effective amount of drug to be incorporated in or released by the system. However, the amount of drug present in the reservoir is generally non-limited and it is an amount equal to or larger than the amount of drug that on its release from the system is effective for bringing about the drug's effects. Thus, the amount of agent present in the reservoir, whether dissolved, partially dissolved or undissolved is generally an amount equal to or larger than the amount of an agent that on its release from the device is effective for being about the agent's effect. For example, the amount of anti-fertility agent present in the reservoir of an intrauterine device when the device is used for a predetermined period of time to achieve an anti-fertility effect in a potential child-bearing woman is for pregn-4-ene-3,20-dione for a year supply wherein a year is 400 days, and the rate of release from the device is 25 μg/day is 10 mg in the reservoir, at the same rate of release for 2 years a reservoir supply of 20 mg and for 3 years 30 mg. If the rate of release for the same progestational agent is 100 μg/day and the length of the year as before, the reservoir concentration for 1 year is 40 mg, for 2 years 80 mg, and for 3 years 120 mg. The amount of progestational agent present in the reservoir for a 1 year, 2 year, and 3 year device is 80 mg, 160 mg and 240 mg respectively when the rate of release is 200 µg/day. Of course, for shorter periods or longer periods smaller amounts or larger amounts will be present in the reservoir, and the amount will also vary relative to the degree of activity of the progestational agent. Generally, the intrauterine contraceptive device will contain from about 250 nanograms to 10 g of a progestational or estrogenic agent, in a presently preferred amount of 250 nanograms to 5 grams of said steroids, for releasing it at a controlled rate of from about 5 micrograms to 300 micrograms of agent, or larger amounts per day. Of course, devices containing different amounts of agent for use for different time periods such as week, month, and the like, are also readily made by the invention. The above agents are described in *Pharmaceutical Science*, by Remington, Fourteenth Edition, 1970, published by Mack Publishing Co., Easton Pa., and in the *Pharmacological Basis of Therapeutics*, by Goodman and Gilman, Fourth Edition, 1970, published by the MacMillan Co., New York.

The systems of the invention are easily fabricated. When the system is in the form of a matrix with drug distributed therethrough, particles of the drug can be mixed with the copolymer, which can be in the solid, semi-solid, or liquid form at the time, and distributed therethrough by ballmilling, callendering, stirring, shaking or the like. Where the drug is chemically compatible with the monomers used to form the ethylene-vinyl ester copolymer, the drug particles can be added at this earlier stage and the ethylene-vinyl ester matrix formed in situ. The matrix, however made and having the drug particles distributed therethrough, can then be formed to a solid shape by molding, casting, pressing, extruding, drawing or like processes. Thereafter, the matrix can be cross-linked, if desired, for example, by use of irradiation. Alternatively, the matrix can be formed to the desired shape and placed in a bath of the drug or of a solvent solution of the drug which then diffuses into the matrix to provide the system. When the system is a sealed container with walls of ethylene-vinyl ester copolymer and the drug in an interior reservoir, the container can be fabricated in many ways. Preformed hollow shapes of ethylene-vinyl ester copolymer such as tubing, can be filled with drug, alone or dispersed in a suitable vehicle, and the ends sealed with plugs or by heat to form the final system. Alternatively, the drug can be laminated between sheets of the copolymer which can be sealed together with adhesive or by heat. Other encapsulation, bonding and coating techniques conventionally used in the art can be employed. The ability to shape the copolymers into tubes, disks, films, rings and other highly reproducible shapes of controllable composition results in ready fabrication of systems with closely controlled characteristics and overcomes a significant disadvantage of previously described ocular devices. Other standard procedures, as described in *Modern Plastics Encyclopedia*, Volume 46, pages 62 to 70, 1969, well known to those skilled in the art can be used to fabricate the drug delivery device of the invention.

In addition to its ease of fabrication, the system of the invention offers other important advantages. One of these is that diffusion of drugs, through ethylene-vinyl ester copolymers proceeds at a lower rate than through many prior art polymers such as silicone rubber. This is important because it ensures that the rate of drug administration is controlled by diffusion through these copolymers rather than by clearance from the surface of the device. In addition, the copolymers are not known to absorb lipoidal materials at the same rate from the body, as do silicone rubber membranes and some other polymers, and therefore the characteristics of the rate controlling membrane do not vary substantially with time. This permits use of systems for therapeutic programs for a couple of days, a week or more. Another added advantage of the present invention is that the copolymers seemingly do not give rise to unwanted effects when in contact with biological media. One especially important use of the invention is in drug dispensing intrauterine devices for controlling fertility. The reason for this is that it has unexpectedly been found that ethylene-vinyl ester copolymers provide excellent diffusion barriers for the controlled release of progestational and estrogenic agents, such as progesterone and estrogen over a prolonged period of time. Such devices incorporate within their interior a progestational or estrogenic agent, such as progesterone or estrogen which is released by diffusion through the ethylene-vinyl ester copolymer walls of the intrauterine device. The intrauterine contraceptive device is of appropriate size and shape for comfortable insertion and prolonged retention in the uterus. For example, the device can be in the form of a Lippe's Loop as disclosed in U.S. Pat. No. 3,250,271; Shamrock in U.S. Pat. No. 3,077,879; Birnberg Bow in U.S. Pat. No. 3,319,625; and the like. By controlling diffusion of the anti-fertility agent such as progestational or estrogenic agent through the ethylene-vinyl ester copolymer walls of the intrauterine device, fertility can be controlled for long periods of time, for example up to one year, two years, or longer.

The reservoir of the system in one embodiment of the invention, is a matrix that contacts the inner surface of the drug release rate controlling copolymer wall and supplies drug thereto. The reservoir is comprised of a liquid, semi-solid or solid matrix containing drug, and it is a material that is permeable to the passage of drug by diffusion. The matrix can be an organic, inorganic, naturally occurring or synthetic material. Examples of matrix are gelatin, starches, carbohydrates, Irish moss, hydrophilic hydrogels of esters of acrylic acid, modified collagen, silicone oil, corn oil, saline, peanut oil, and like materials. Also, other commercially available matrixes permeable to the passage of drug but at a higher rate of passage than through the wall of the device are suitable for the reservoir of the device. Representative matrixes are set forth in *Remington's Pharmaceutical Science*, pages 246 to 269, 1338 to 1390 and 1627 to 1979, 1970, published by Mack Publishing Company, Easton, Pa. The degree of solubility of various anti-fertility agents in various liquid cores present in reservoir 12a is ascertained by using the above techniques. Typical examples of solubilities are as follows: 6-chloro-17-hydroxypregna-4,6-diene-3,20-dione acetate practically insoluble in water; 17β-hydroxy-6α-methyl-17-(1-propynl)-androst-4-3n3-3one slightly soluble in acetone; 9β,10α-pregna-4,6-diene-3,20-dione slightly soluble in distilled water; 17-hydroxy-17α-pregn-4-en-20-yn-3-one slightly soluble in alcohol and slightly soluble in vegetable oil, 19-nor-17α-pregn-4-en-20-yne-3β-17-dioldiacetate sparingly soluble in fixed oil, 17-hydroxy-6α-methylpregn-4-ene-3,20-dione acetate sparingly soluble in methanol, 17-hydroxy-19-nor-17α-pregn-4-en-20yn-3-one sparingly soluble in vegetable oil, 17-β-estradiol sparingly soluble in vegetable oil, ethinyl estradiol soluble in various vegetable oils, and the like.

The following examples are merely illustrative of the present invention and they should not be considered as limiting the scope of the invention in any way, as these examples and other equivalents thereof will become apparent to those versed in the art in the light of the present disclosure, drawings, and the accompanying claims.

EXAMPLE 1

An intrauterine anti-fertility dispensing device shaped like a tear drop and comprising a reservoir comprising a liquid carrier containing an anti-fertility agent and permeable to the passage of anti-fertility agent is manufactured as follows: first, a reservoir comprised of a liquid core consisting of 11% by weight of progesterone and 10% by weight of barrium sulfate in a mixture of 3 parts by weight of liquid silicone oil number 382 and 1 part by weight of medical grade fluid silicone oil number 360 are thoroughly mixed in a standard laboratory v-blender to yield a liquid core. The progesterone is sparingly soluble in the liquid core. Next, an aliquot of the liquid core is injected into a section of medical grade ethylene-vinyl methyl acetate copolymer tubing having an outside diameter of 0.110 inches and an inside diameter of 0.70 inches and the ends of the tubing adhesively sealed. The tubing is then placed into the lower half of a two piece tear-drop shaped mold to yield the intrauterine device. The device will release a contraceptively effective amount of progesterone per day in an adult woman weighing from 35 kg to 90 kg.

EXAMPLE 2

Milled crystals of progesterone, 60 milligrams in corn oil, are placed within a tube 1.5 cm long, having an inside diameter of 0.125 inch, a wall thickness of 4 mil, and formed of ethylene-vinyl methyl acetate copolymer having an ester content of 18 mol%. The tube ends are heat sealed and the unit used for conception control by attachment to an intrauterine device, for example, a Lippe's Loop. The device is inserted into the uterine lumen through the cervix. The device controls fertility by releasing 5 μg/hr/cm² of progesterone to the uterine cavity of an adult woman.

EXAMPLE 3

Milled crystals of progesterone are mixed with ethylene-vinyl methylacetate copolymer having a vinyl methyl acetate content of 22% by weight and the mixture ballmilled for 20 minutes to provide a uniform distribution of steroid throughout the copolymeric reservoir. Thereafter, the resulting mixture is shaped and size adapted as a triangle for insertion and retention in the uterus.

EXAMPLE 4

An intrauterine contraceptive anti-fertility administrating device having the shape of an open circle with one end extended around the other end and receded from it with the wall of the circle formed of a release rate controlling material permeable to the passage of the agent and surrounding a reservoir comprising of a liquid core containing the agent is fabricated as follows: first, a section of medical grade ethylene-vinyl methylacetate copolymer tubing is washed with diluted methanol for at least 72 hours, rinsed with water, and then air dried.

Next, a core material is prepared as a homogenous mixture consisting of 11% by weight of progesterone N.F., 10% by weight of barium sulfate, U.S.P., 19.5% by weight of Dow-Corning 360 Medical Fluid, a water white polydimethylsiloxane fluid, and 59.25% by weight of Dow-Corning Silastic 382 Medical Grade Elastomer, a fluid polysiloxane polymer by thoroughly blending the ingredients for 59.25% by weight of Dow-Corning Silastic 382 Medical Grade Elastomer, a fluid polysiloxane polymer by thoroughly blending the ingredients for about 10 to 12 hours. Next, the core material is injected into precut lengths of the washed copolymer tube and the devices formed by placing the filled tubing in a mold having a female portion containing a cavity which corresponds to the shape of the device. When the mold is closed, the male portion of the mold forms the top of the device. The clearance between the male member and the female member is sufficiently small, so that closing the molds and applying heat thereto forms the predetermined device. The device contains 20 mg of progesterone for releasing it at a rate of 5 μg/hr for 2 years.

EXAMPLE 5

Following the procedure of Examples 1 through 4, an intrauterine device consisting essentially of a liquid core and a steroid selected from the group consisting of norgestrel and estradiol is surrounded with a release rate controlling copolymer of ethylene-vinyl methylacetate copolymer for releasing 3.5 μg/day of norgestrel from the device having a film 4 mil thick and an 18 mol% content of ethylene-vinyl acetate copolymer, or 12 μg/day of estradiol to a fertile uterus for the management of contraception.

In summary, it will be readily appreciated that the present invention contributes to the art unobvious intrauterine delivery devices having wide and practical application by the invention's use of ethylene-vinyl ester copolymer. As noted supra, it has now been found that ethylene-vinyl ester copolymer can be used for the controlled release of many intrauterine releasable drugs. In contrast, highly crystalline materials such as polyethylene or materials such as partially hydrolyzed polyvinyl acetate having a profusion of side groups, do not lend themselves to use in like environments. And while the invention has been described and pointed out in detail and with reference to operative embodiments thereof, it will be understood that those skilled in the art will appreciate that various changes, modifications, substitutions and omissions can be made without departing from the spirit of the invention. It is intended, therefore, that the invention embrace these equivalents within the scope of the claims which follow.

I claim:

1. An intrauterine system for the controlled administration of an anti-fertility agent in an effective amount to the uterus of a warm blooded mammal, said system comprising a flexible body of a copolymeric material containing a progestational steroid capable of diffusing through said copolymeric material, said body sized, shaped and adapted for comfortable insertion and retention in the uterine lumen, and wherein said material comprises a copolymer of the following formula:

wherein R is a member selected from the group consisting of a lower alkyl group of 2 to 7 carbons and phenyl, m is (4 to 80)% by weight, n is (100-n)% by weight, and which copolymer has a melt index of about 0.1 to 1000 grams per ten minutes.

2. The intrauterine system according to claim 1, wherein the copolymer contains from 250 nanograms to 5 grams of progestational steroid, has a frequency of acyloxy groups on the copolymeric backbone of 1/200 to 1/35, and a density of 0.120 to 1.25.

3. The intrauterine system according to claim 1, wherein the progestational steroid is progesterone and the copolymer has a vinyl ester content of 4 to 50% by weight and a melt index of 0.5 to 250 grams per ten minutes.

4. An intrauterine system for the controlled administration of an anti-fertility agent in an effective amount to the uterus of a warm-blooded mammal, said system comprising a body of copolymeric material surrounding a reservoir containing an anti-fertility progestational steroid capable of diffusing through said copolymeric material, said body sized, shaped and adapted for insertion and retention in the uterine lumen for a prolonged period of time, and wherein said material comprises a copolymer of the following formula:

wherein the copolymer has a vinyl ester content m of about (4 to 80)% by weight, an ethylene content n of (100-m)%, a melt index of about 0.1 to 1000 grams per ten minutes, and R is a member selected from the group consisting of lower alkyl of 2 to 7 carbon atoms and phenyl.

5. The intrauterine system according to claim 4 wherein the copolymer has a frequency of acyloxy groups on the copolymeric backbone of 1/200 to 1/35, a density of 0.120 to 1.25, and the reservoir is a container with from 250 nanograms to 5 grams of progestational steroid housed therein.

6. The intrauterine system according to claim 4, wherein the progestational steroid is progesterone and the copolymer has a vinyl ester content of 4 to 50% by weight and a melt index of 0.5 to 250 grams per ten minutes.

7. An intrauterine system for the controlled administration of an anti-fertility agent in an effective amount to the uterus of a warm-blooded mammal, said system comprising a flexible body of a copolymeric material containing an estrogenic steroid capable of diffusing through said copolymer, said body sized, shaped and adapted for insertion and retention for a prolonged period of time in the uterine cavity, and wherein said material comprises a copolymer of the following formula:

and wherein the copolymer has a melt index of about 0.1 to 1000 grams per ten minutes, R is a member selected from the group consisting of alkyl of 2 to 7 carbon atoms and phenyl, m is (4 to 80)% by weight and n is (100-n)% by weight.

8. The intrauterine system according to claim 7, wherein the copolymer contains from 250 nanograms to 5 grams of estrogenic steroid, m has a frequency on the copolymeric backbone of 1/200 to 1/35, and the copolymer has a density of 0.920 to 1.25.

9. An intrauterine system for the controlled administration of an anti-fertility agent in an effective amount to the uterus of a warm-blooded mammal, said system comprising a copolymeric material surrounding a reservoir containing an anti-fertility estrogenic steroid capable of diffusing through the copolymer, said system further being sized, shaped and adapted for insertion and retention in the uterus for a prolonged period of time, and wherein said copolymer has the following formula:

wherein R is a member selected from the group consisting of alkyl of 2 to 7 carbon atoms and phenyl, m is (4 to 80)% by weight, and which copolymer has a melt index of about 0.1 to 1000 grams per ten minutes is permeable to the passage of the steroid with the steroid dissolving in and passing through the ethylene-vinyl ester copolymer.

10. The intrauterine system according to claim 9, wherein m has a frequency on the copolymeric backbone of 1/200 to 1/35, the copolymer has a density of 0.920 to 1.25, and the reservoir is a container with from 250 nanograms to 5 grams of non-toxic, anti-fertility estrogenic steroid housed therein.

11. An intrauterine system for the controlled administration of drug in a therapeutically effective amount to the uterus of a warm-blooded mammal comprising a flexible body of a copolymeric material containing a drug capable of diffusing through the material in a therapeutically effective rate, said system sized, shaped and adapted for insertion and retention in the uterus for a prolonged period of time, and wherein said copolymer comprises an ethylene-vinyl alkyl substituted acetate having a vinyl alkyl acetate content of about 4 to 80% by weight, a melt index of about 0.01 to 1000 grams per ten minutes, and the alkyl group has 2 to 7 carbon atoms with the copolymer permeable to drug, which drug dissolves in and passes through the copolymer by diffusion.

12. An intrauterine system for the controlled administration of drug in a therapeutically effective amount to the uterus of a warm-blooded mammal comprising a copolymeric material surrounding a reservoir containing a drug capable of diffusing through the copolymer at an effective rate, said system sized, shaped and adapted for easy insertion and prolonged relation in the uterus, and wherein said copolymer comprises an ethylene-vinyl alkyl substituted acetate having a vinyl alkyl acetate content of about 4 to 80% by weight, a melt index of about 0.1 to 1000 grams per ten minutes and the alkyl group has 2 to 7 carbon atoms, with the copolymer permeable to drug which drug dissolves in and passes through the copolymer by diffusion.

* * * * *